United States Patent [19]
Marx et al.

[11] 4,064,240
[45] Dec. 20, 1977

[54] 21-CYCLIC ACETALS OF STEROIDAL 21-ALDEHYDES AND METHODS OF PREPARATION

[75] Inventors: Michael Marx, Sunnyvale; Denis John Kertesz, Menlo Park, both of Calif.

[73] Assignee: Syntex (U.S.A.) Inc., Palo Alto, Calif.

[21] Appl. No.: 742,980

[22] Filed: Nov. 17, 1976

[51] Int. Cl.² .................. C07J 71/00; A61K 31/58
[52] U.S. Cl. .................. 424/241; 260/239.55 D
[58] Field of Search ............. 424/241; 260/239.55 C, 260/239.55 D

[56] References Cited

U.S. PATENT DOCUMENTS

| 3,732,210 | 5/1973 | Stache et al. | 260/239.55 R |
| 3,761,498 | 9/1973 | Villax | 260/239.55 C |

*Primary Examiner*—Elbert L. Roberts
*Attorney, Agent, or Firm*—Gerard A. Blaufarb; William B. Walker

[57] ABSTRACT

21-Cyclic acetals of steroids of the corticoid series are prepared from the corresponding 21-hydroxy steroids. The products have utility as anti-inflammatory agents.

22 Claims, No Drawings

21-CYCLIC ACETALS OF STEROIDAL 21-ALDEHYDES AND METHODS OF PREPARATION

SUMMARY OF THE INVENTION

The present invention relates to 21-cyclic acetals of steroidal 21-aldehydes having anti-inflammatory activity. More particularly, the present invention relates to compounds of the formula

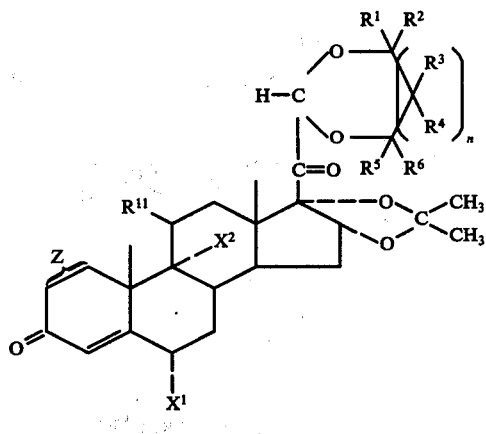

wherein:

$n$ is 0 or 1;

each of $R^1 - R^6$ is independently hydrogen or lower alkyl containing 1 to 4 carbon atoms and when $n$ is 0, any two of $R^1 - R^6$ on adjacent carbon atoms, taken together, are lower alkylene containing 3 to 5 carbon atoms;

$R^{11}$ is chloro or hydroxy;

$X^1$ and $X^2$ are independently hydrogen, chloro or fluoro; with the proviso that when $R^{11}$ is chloro, $X^2$ is chloro; and Z is a single or double bond.

Preferred subclasses of compounds within the class defined by formula (I) are represented by the formulas:

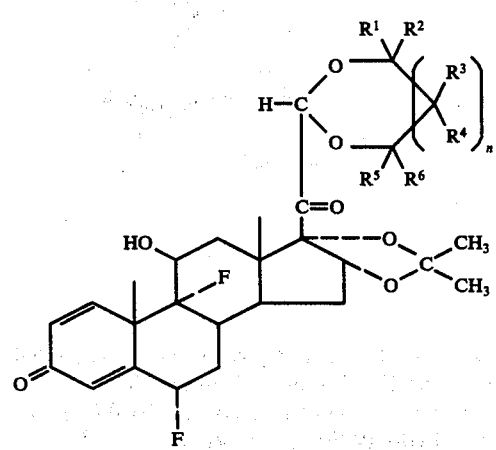

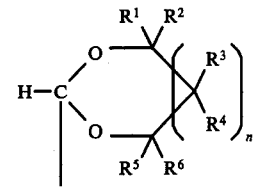

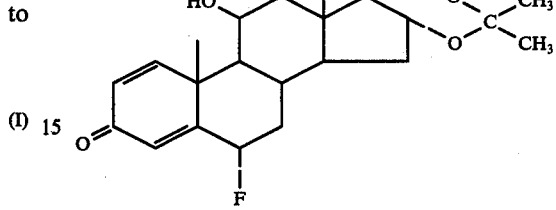

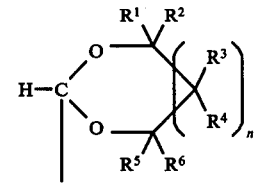

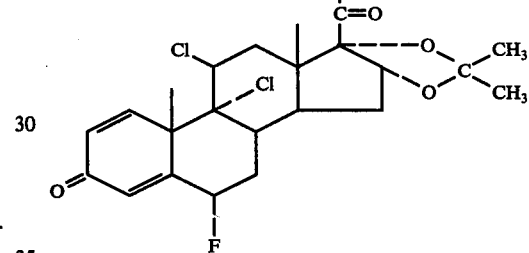

wherein $R^1 - R^6$ and $n$ are as defined hereinabove.

Preferred compounds within the above defined subclasses are those wherein:

a. all of $R^1 - R^6$ are hydrogen;
b. one of $R^1 - R^6$ is a lower alkyl group containing 1 to 4 carbon atoms and the other R groups are hydrogen; and
c. two of $R^1 - R^6$ are independently lower alkyl groups containing 1 to 4 carbon atoms and other R groups are hydrogen.

The compounds of the instant invention are potent topical anti-inflammatory agents. Although the instant compounds exhibit low systemic activity in the rat as measured in standard assays, e.g. Rat Thymolytic Assay and the Anti-inflammatory Assay Utilizing Carrageenan-induced Rat Paw Edema, they exhibit high topical activity in humans as measured in the Stoughton-McKenzie Assay (Human Vasoconstrictor Assay). In spite of the fact that systemic effects such as adrenal atrophy, mineralocorticoid effects and collagen disorders may be produced by large doses of the instant compounds if administered for long periods of time, the favorable topical/systemic activity ratio of the compounds permits the use of such small doses that these systemic effects are minimized. This combination of high topical anti-inflammatory activity coupled with negligible systemic activity renders the instant compounds highly suitable for the alleviation of inflammatory disorders.

Accordingly, in view of the aforementioned activity of the subject compounds, the present invention further relates to pharmaceutical compositions useful for treating inflammatory disorders. Such compositions comprise an effective amount of a compound selected from those represented by formula (I) in admixture with a pharmaceutically acceptable non-toxic carrier.

Suitable carriers or medicament vehicles for topical application of the novel steroids of the instant invention include creams, ointments, lotions, emulsions, solutions, and the like. For example, a suitable ointment for topical application of compounds of the instant invention contains 15 to 45 wt. percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and the mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms (e.g., stearic acid, palmitic acid, behenic acid), a fatty acid amide (e.g., oleamide, palmitamide, stearamide, behenamide), a fatty acid ester having from 16 to 24 carbon atoms (e.g., sorbitol monostearate polyethylene glycol monostearate, polypropylene glycol monostearate) or the corresponding monoester of other fatty acids such as oleic acid and palmitic acid; and 0 to 20 wt. percent of a penetrant such as dimethyl sulfoxide, dimethylacetamide, dimethylformamide, and the like.

The concentration of cortical steroid in pharmaceutical compositions suitable for topical application will vary depending upon the particular activity of the steroid used in conjunction with the condition and subject to be treated. In general, topical preparations containing 0.005 to 1% by weight of the active steroid are advantageously employed.

The present invention still further relates to a method for treating symptoms associated with inflammatory disorders, which method comprises administering an effective amount of a compound selected from those represented by formula (I), or a pharmaceutical composition incorporating such a compound as an active ingredient.

As used in the Specification and appended claims, unless specified to the contrary, the following definitions apply:

The broken line (---) used in the depicted formulas indicates that the substituent attached to those positions is in the α configuration.

The unbroken line (—) used in the depicted formulas indicates that the substituent attached to those positions is in the β configuration.

The term "lower alkyl" refers to a straight or branched chain monovalent substituent consisting solely of carbon and hydrogen, containing no unsaturation and having from 1 to 4 carbon atoms. Examples of lower alkyl groups are methyl, ethyl, n-propyl, isopropyl, n-butyl, sec-butyl, isobutyl, and tert-butyl.

The term "lower alkylene" refers to a straight chain divalent substituent consisting solely of carbon and hydrogen, containing no unsaturation and having from 3 to 5 carbon atoms.

DETAILED DESCRIPTION

The present invention, in a further aspect, is directed to several processes for the preparation of compounds of Formula (I).

A first process for preparing the compounds of the instant invention can be schematically represented by the following reaction sequence:

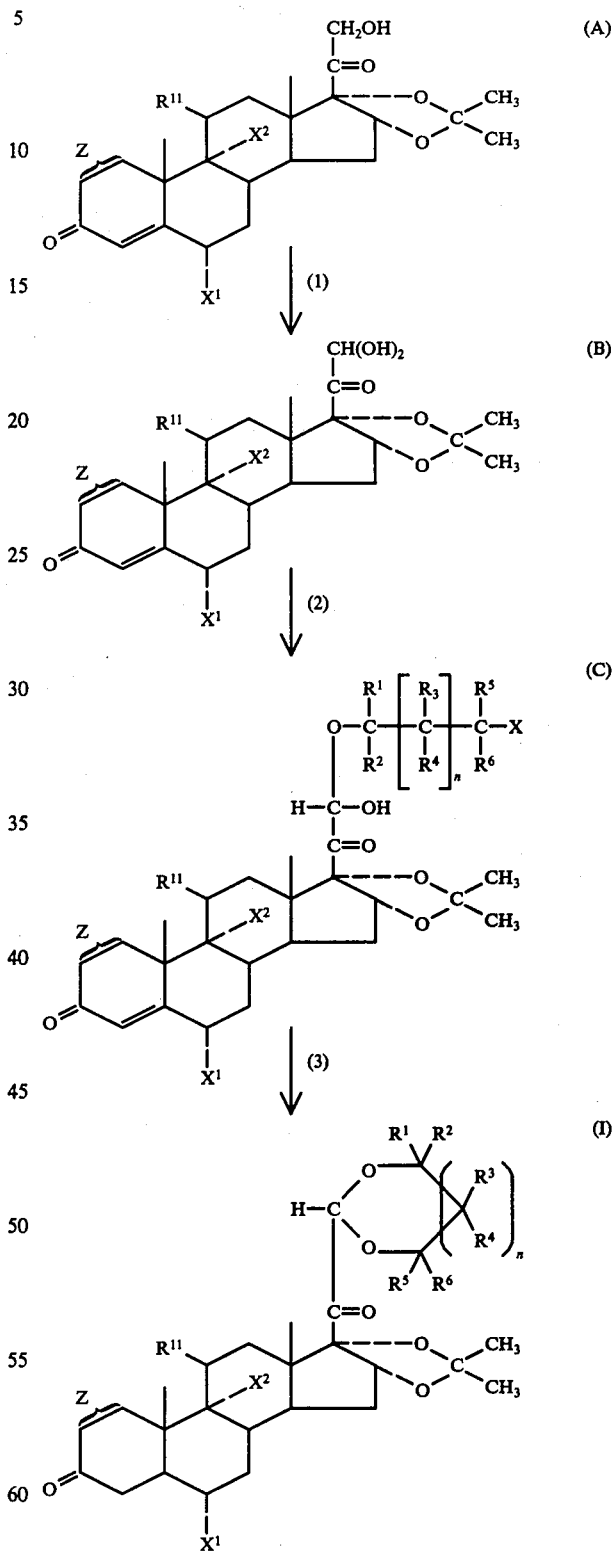

wherein $R^1 - R^6$, $R^{11}$, $X^1$, $X^2$, Z and n are as defined hereinabove and X is bromo, chloro or iodo.

Step 1 of the process can be conveniently effected by treating a 21-hydroxy steroid of formula (A) with air or oxygen in the presence of an oxidation catalyst, preferably copper (II) acetate. Typically, this treatment is conducted in methanol at temperatures in the range of about 5° to 30° C., preferably at about 20° C, for about from 30 minutes to 6 hours, preferably for about 2 hours. Typically, a mole ratio of catalyst to compound of formula (A) of about from 1:4 to 1:20, preferably about from 1:8 is used.

The starting materials of formula (A) are either available commercially or can be prepared according to known procedures. Information concerning the preparation of 21-hydroxy steroids suitable for use in the preparation of the compounds of the instant invention can be obtained from U.S. Pat. Nos. 3,048,581 and 3,126,375; and from Fried et al, J. Am. Chem. Soc., 802, 338 (1958) and Mills et al., J. Am. Chem. Soc., 82, 3399 (1960). Additional information concerning the preparation of 21-hydroxy steroids can be found for example, in U.S. Pat. Nos. 2,894,963, 3,013,033, and 3,119,748; and Edwards et al., Proc. Chem. Soc. (London), p. 87 (1959), Edwards et al., J. Am. Chem. Soc., 82, 2318 (1960), and Taub et al., J. Am. Chem. Soc., 80, 4435 (1958).

Step 2, preparation of the 21-aldehyde hemiacetal, is conveniently effected by heating the 21-aldehyde hydrate of formula (B) under vacuum at a temperature of about from 100° to 130° C, preferably at about 110° C, for about from 30 minutes to 6 hours (preferably about 1 hour) and thereafter treating the resultant 21-aldehyde with a halohydrin having the desired $R^1$ - $R^6$ substituents. Treatment of the 21-aldehyde with a halohydrin can be effected in the absence or presence of an inert organic solvent at temperatures in the range of about from 10° to 50° C, preferably at about 20° C. for about from 30 minutes to 6 hours, preferably about 1 hour. A mole ratio of 21-aldehyde to halohydrin of about from 1:2 to 1:100, preferably about from 1:20 to 1:40 is used. Suitable inert organic solvents that can be used include, for example, methylene chloride and benzene.

The halohydrins used in step 2 are either available commercially or can be prepared according to procedures described in the literature.

Step 3, cyclization of the 21-aldehyde hemiacetal, can be conveniently effected by treating the compound of formula (C) with a base in the presence of a protic solvent. Typically, this treatment is conducted at temperatures in the range of about 10° to 50° C, preferably at about 20° C, for about from 1 to 20 hours, preferably about 3 hours. Suitable bases which can be used include, for example, alkali metal alkoxides and alkali metal hydroxides (sodium hydroxide being preferred). Suitable solvents which can be used include, for example, water, alcohols, and mixtures thereof (aqueous ethanol being preferred). A mole ratio of 21-aldehyde hemiacetal (C) to base of about from 1:2 to 1:20, preferably about from 1:5 is used.

A second process for preparing the compounds of the instant invention can be schematically represented by the following reaction sequence:

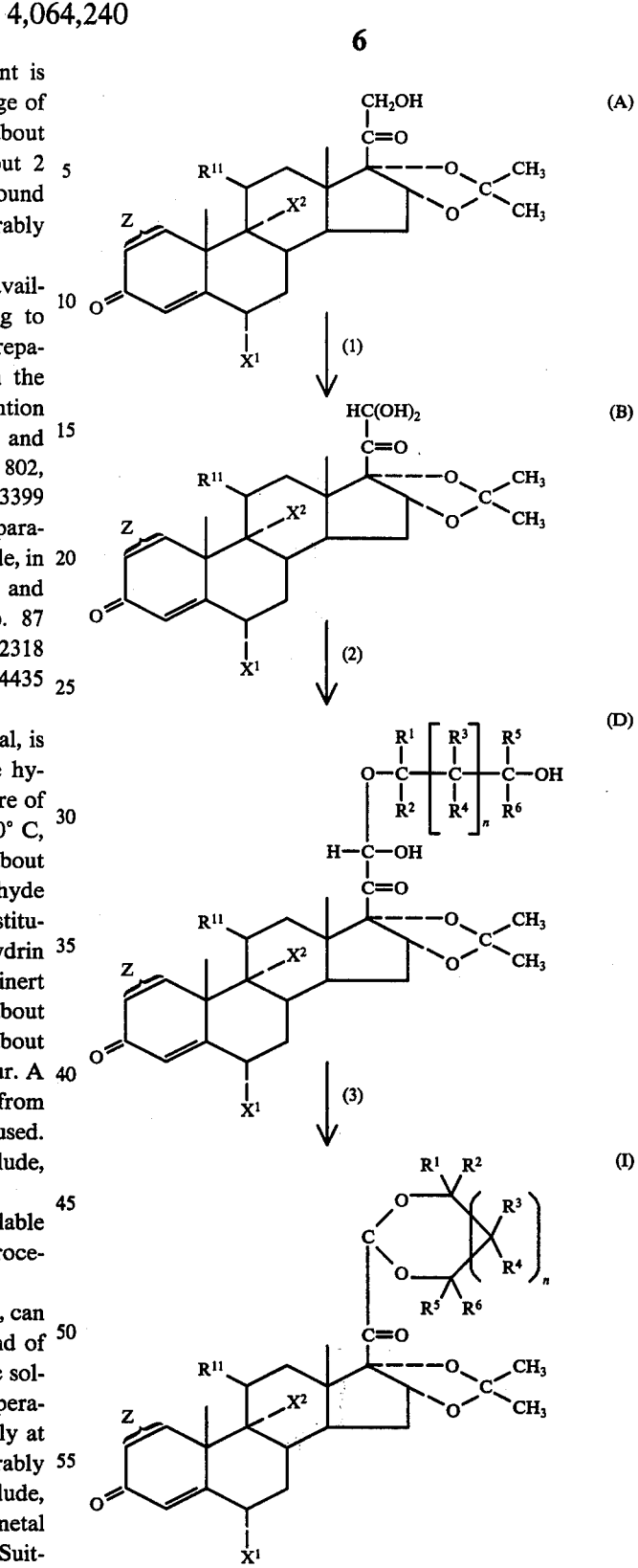

wherein $R^1$ - $R^6$, $R^{11}$, $X^1$, $X^2$, Z and n are as defined hereinabove.

Step 1 of the process is effected in the manner described in the previous process.

Step 2, preparation of the 21-aldehyde hemiacetal, is conveniently effected by heating the 21-aldehyde hydrate of formula (B) under vacuum at a temperature of about from 100° to 130° C, preferably at about 110° C, for about from 30 minutes to 6 hours (preferably about 1 hour) and thereafter treating the resultant 21-aldehyde with a dihydric alcohol having the desired $R^1 - R^6$ substituents. Treatment of the 21-aldehyde with a dihydric alcohol can be effected in the absence or presence of an inert solvent at temperatures in the range of about from 10° to 50° C, preferably at about 20° C, for about from 30 minutes to 6 hours, preferably about 1 hour. A mole ratio of 21-aldehyde to dihydric alcohol of about from 1:2 to 1:100, preferably about from 1:20 to 1:40 is used. Suitable inert organic solvents that can be used include, for example, methylene chloride and benzene.

The dihydric alcohols used in step 2 are either available commercially or can be prepared according to procedures described in the literature.

Step 3, cyclization of the 21-aldehyde hemiacetal, can be conveniently effected by treating the compound of formula (D) in the presence of base, with a reagent capable of converting a hydroxy group to a suitable leaving group such as a halide (e.g., a chloride or bromide) or a sulfonate ester (e.g. methane sulfonate or p-toluenesulfonate). Conversion of the hydroxy group to a halide can be accomplished with a halogenating agent such as thionyl chloride or thionyl bromide; conversion to a sulfonate ester can be accomplished using methanesulfonyl chloride or p-toluenesulfonyl chloride. Suitable bases that can be used include, for example, triethylamine and pyridine. The 21-aldehyde hemiacetal may be cyclized either employing the base as a solvent or in the presence of an inert organic solvent such as methylene chloride or benzene, at temperatures in the range of about from −20° to 10° C. (preferably at about 0° C) for about from 1 to 12 hours (preferably about 6 hours) using 2:1 to 10:1 moles of thionyl halide sulfonyl halide) and 10:1 to 50:1 moles of base per mole of hemiacetal.

The respective product of each process step described hereinabove, can be separated and/or isolated prior to its use as starting material for subsequent steps. Separation and isolation can be effected by any suitable or purification procedure such as, for example, evaporation, crystallization, column chromatography, thin-layer chromatography, distillation, etc. Specific illustrations of typical separation and isolation procedures can be had by reference to the appropriate examples described hereinbelow; however, other equivalent separation procedures could, of course, also be used. Also, it should be appreciated that where typical reaction conditions (e.g. temperatures, mole ratios, reaction times) have been given, conditions both above and below these ranges can also be used, though generally less conveniently.

The following specific description is given to enable those skilled in the art to more clearly understand and practice the present invention. It should not be considered as a limitation upon the scope of the invention but merely as illustrative and representative thereof.

EXAMPLE 1

This example illustrates step 1 of the first and second processes described for preparing the compounds of the invention. In this example, a solution of 0.68 g. of cupric acetate hydrate in 40 ml. methanol is added to a slurry of 12.0 g. of 6α,9α-difluoro-11β,16α,17α,21-tetrahydroxypregna-1,4-diene-3,20-dione-16,17-acetonide in 130 ml. of dry methanol. Air is then sparged through the mixture for 2 hours. Thereafter, the mixture is evaporated to dryness and the residue is taken up in ethyl acetate and washed with water and then with a dilute aqueous solution of potassium bicarbonate and then again with water. The solution is evaporated to dryness and the resulting residue is then dissolved in acetone. The acetone solution is diluted with a substantial volume of water whereupon the resulting precipitate is collected by filtration and dried under vacuum to yield 6α,9α-difluoro-11β,16α,17α,21,21-pentahydroxypregna-1,4-diene-3,20-dione-16,17-acetonide.

Similarly, by following the above procedure, but replacing 6α,9α-difluoro-11β,16α,17α,21-tetrahydroxypregna-1,4-diene-3,20-dione-16,17-acetonide with other 21-hydroxy steroids enumerated in Table 1, is productive of the corresponding steroidal 21-aldehyde hydrates enumerated in Table 2:

TABLE 1

(structure shown with substituents $R^{11}$, $Z$, $X^1$, $X^2$; CH₂OH—C=O group with 16,17-acetonide)

| Z | $R^{11}$ | $X^1$ | $X^2$ |
|---|---|---|---|
| U | HO | F | H |
| S | HO | F | F |
| U | HO | F | H |
| U | Cl | F | Cl |
| U | HO | F | Cl |
| U | HO | H | F |
| S | HO | H | H |
| U | HO | H | H |
| U | HO | Cl | H |

NOTE - U = unsaturation; S = saturation.

TABLE 2

(structure shown with substituents $R^{11}$, $Z$, $X^1$, $X^2$; CH(OH)₂—C=O group with 16,17-acetonide)

| Z | $R^{11}$ | $X^1$ | $X^2$ |
|---|---|---|---|
| U | HO | F | H |
| S | HO | F | F |
| U | HO | F | H |
| U | Cl | F | Cl |
| U | HO | F | Cl |
| U | HO | H | F |
| S | HO | H | H |
| U | HO | H | H |
| U | HO | Cl | H |

NOTE - U = unsaturation; S = saturation.

EXAMPLE 2

This example illustrates steps 2 and 3 of the first process described for preparing the compounds of the invention.

In this example, 200 mg. of 6α,9α-difluoor-11β,16α,17α, 21,21-pentahydroxypregna-1,4-diene-3,20-dione-16,17-acetonide is heated under high vacuum in an oil bath at 100° C. for 1 hour. Thereafter, the resultant 21-aldehyde is cooled to room temperature and 1 ml. of 2-bromoethanol is added. After stirring the mixture for 30 minutes at room temperature, a grey/brown slurry is obtained. Thereafter, 10 ml. of ethanol and 1 ml. of aqueous 2 N sodium hydroxide is added to the slurry and stirring is continued over-night. The mixture is then concentrated to one-half its volume under reduced pressure and the resulting solution of crude steroidal 21-cyclic acetal is treated with 100 ml. of water, cooled in an ice bath and then filtered. The collected solid is dried under vacuum to yield 83 mg. of 6α,9α-difluoro-11β,16α,17α, 21,21-pentahydroxypregna-1,4-diene-3,20-dione-16,17-acetonide-21,21-ethylene acetal, m.p. 270°–273° C.

EXAMPLE 3

Following the procedure of Example 2, using equivalent amounts of appropriate starting materials enumerated in Tables 3 and 4, is productive of the corresponding steroidal 21-cylcic acetals enumerated in Table 5:

TABLE 3

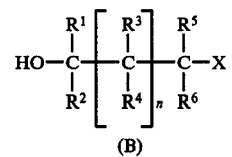

(A)

| Z | $R^{11}$ | $X^1$ | $X^2$ |
|---|---|---|---|
| U | HO | F | F |
| U | HO | F | H |
| S | HO | F | F |
| U | HO | F | H |
| U | Cl | F | Cl |
| U | HO | F | Cl |
| U | HO | H | F |
| S | HO | H | H |
| U | HO | H | H |
| U | HO | Cl | H |

NOTE - U = unsaturation; S = saturation.

TABLE 4

$$HO-\underset{R^2}{\overset{R^1}{\underset{|}{C}}}-\left[\underset{R^4}{\overset{R^3}{\underset{|}{C}}}\right]_n-\underset{R^6}{\overset{R^5}{\underset{|}{C}}}-X$$

(B)

| n | $R^1/R^2$ | $R^3/R^4$ | $R^5/R^6$ | X |
|---|---|---|---|---|
| 0 | H/H | | H/H | Br; Cl; I |
| 0 | $C_1$/H | | H/H | Br; Cl; I |
| 0 | $C_2$/H | | H/H | Br; Cl |
| 0 | $C_3^n$/H | | H/H | I |
| 0 | $C_3^i$/H | | H/H | Br |
| 0 | $C_4^n$/H | | H/H | Br; Cl |
| 0 | H/H | | $C_1$/H | Br; Cl; I |
| 0 | H/H | | $C_2$/H | Br; Cl |
| 0 | H/H | | $C_3^i$/H | Br; Cl |
| 0 | $C_1$/H | | $C_1$/H | Br; Cl |
| 0 | $C_3^n$/H | | $C_3^n$/H | Br |
| 0 | $C_3^i$/H | | $C_3^i$/H | Br; Cl; I |
| 0 | $C_4^n$/H | | $C_4^n$/H | Br; Cl |
| 0 | $C_1$/H | | $C_2$/H | Br |
| 0 | $C_1$/H | | $C_3^i$/H | Br; Cl |
| 0 | $C_3^i$/H | | $C_1$/H | Cl |
| 0 | $(CH_2)_3$/H | | seeR$^1$/H | Cl |
| 0 | $(CH_2)_4$/H | | seeR$^1$/H | Cl |
| 1 | H/H | H/H | H/H | Br; Cl; I |
| 1 | $C_1$/H | H/H | H/H | Br; Cl |
| 1 | $C_2$/H | H/H | H/H | Cl |
| 1 | $C_3^n$/H | H/H | H/H | Cl |
| 1 | $C_4^n$/H | H/H | H/H | Cl; I |

TABLE 4-continued $$HO-\underset{R^2}{\overset{R^1}{\underset{|}{C}}}-\left[\underset{R^4}{\overset{R^3}{\underset{|}{C}}}\right]_n-\underset{R^6}{\overset{R^5}{\underset{|}{C}}}-X$$

(B)

| n | $R^1/R^2$ | $R^3/R^4$ | $R^5/R^6$ | X |
|---|---|---|---|---|
| 1 | H/H | $C_1$/H | H/H | Br; Cl |
| 1 | H/H | $C_2$/H | H/H | Br; Cl |
| 1 | H/H | $C_3^n$/H | H/H | I |
| 1 | H/H | $C_3^i$/H | H/H | Cl |
| 1 | H/H | $C_4^n$/H | H/H | Br; Cl |
| 1 | H/H | H/H | $C_1$/H | Br; Cl |
| 1 | H/H | H/H | $C_2$/H | Cl |
| 1 | H/H | H/H | $C_4^n$/H | Cl |
| 1 | H/H | $C_1$/$C_1$ | H/H | Br; Cl |
| 1 | H/H | $C_2$/$C_2$ | H/H | Br; Cl |
| 1 | H/H | $C_3^i$/$C_3^i$ | H/H | Cl |
| 1 | H/H | $C_1$/$C_3^n$ | H/H | Br; Cl; I |
| 1 | H/H | $C_1$/$C_3^i$ | H/H | Cl |
| 1 | H/H | $C_2$/$C_3^i$ | H/H | Br |
| 1 | H/H | $C_2$/$C_4^n$ | H/H | Cl |
| 1 | $C_1$/H | $C_1$/H | H/H | Br; Cl |
| 1 | $C_1$/H | H/H | $C_1$/H | Cl |
| 1 | $C_2$/H | H/H | $C_1$/H | Cl |
| 1 | $C_3^n$/H | H/H | $C_3^n$/H | Br |

NOTE - $C_1$ = methyl; $C_2$ = ethyl; $C_3^n$ = n-propyl; $C_3^i$ = isopropyl; $C_4^n$ = n-butyl.

TABLE 5

6α-fluoro-11β,16α,17α,21,21-pentahydroxypregna-1,4-diene-3,20-dione-16,17-acetonide-21,21-ethylene acetal, 6α,9α-difluoro-11β,16α,17α,21,21-pentahydroxypregn-4-ene-3,20-dione-16,17-acetonide-21,21-ethylene acetal, 6α-fluoro-11β,16α,17α,21,21-pentahydroxypregn-4-ene-3,20-dione-16,17-acetonide-21,21-ethylene acetal, 9α,11β-dichloro-6α-fluoro-16α,17α,21,21-tetrahydroxypregna-1,4-diene-3,20-dione-16,17-acetonide-21,21-ethylene acetal, 9α-chloro-6α-fluoro-11β,16α,17α,21,21-pentahydroxypregna-1,4-diene-3,20-dione-16,17-acetonide-21,21-ethylene acetal, 9α,fluoro-11β,16α,17α,21,21-pentahydroxypregna-1,4-diene-3,20-dione-16,17-acetonide-21,21-ethylene acetal, 11β,16α,17α,21,21-pentahydroxypregn-4-ene-3,20-dione-16,17acetonide-21,21-ethylene acetal, 11β,16α,17α,21,21-pentahydroxypregna-1,4-diene-3,20-dione-16,17-acetonide-21,21-ethylene acetal, 6α-chloro-11β,16α,17α,21,21-pentahydroxypregna-1,4-diene-3,20-dione-16,17-acetonide-21,21-ethylene acetal, 6α,9α-difluoro-11β,16α,17α,21,21-pentahydroxypregna-1,4-diene-3,20-dione-16,17-acetonide-21,21-(1,2-propylene) acetal, 6α,9α-difluoro-11β,16α,17α,21,21-pentahydroxypregna-1,4-diene-3,20-dione-16,17-acetonide-21,21-(1,2-butylene) acetal, 6α,9α-difluoro-11β,16α,17α,21,21-pentahydroxypregna-1,4-diene-3,20-dione-16,17-acetonide-21,21-(1,2-pentylene) acetal, 6α,9α-difluoro-11β,16α,17α,21,21-pentahydroxypregna-1,4-diene-3,20-dione-16,17-acetonide-21,21-(3-methyl-1,2-butylene) acetal, 6α,9α-difluoro-11β,16α,17α,21,21-pentahydroxypregna-1,4-diene-3,20-dione-16,17-acetonide-21,21-(1,2-hexylene) acetal, 6α-fluoro-11β,16α,17α,21,21-pentahydroxypregna-1,4-diene-3,20-dione-16,17-acetonide-21,21-(1,2-propylene) acetal, 6α-fluoro-11β,16α,17α,21,21-pentahydroxypregna-1,4-diene-3,20-dione-16,17-acetonide-21,21-(1,2-butylene) acetal, 6α-fluoro-11β,16α,17α,21,21-pentahydroxypregna-1,4-diene-3,20-dione-16,17-acetonide-21,21-(1,2-pentylene) acetal, 6α-fluoro-11β,16α,17α,21,21-pentahydroxypregna-1,4-diene-3,20-dione-16,17-acetonide-21,21-(3-methyl-1,2-butylene) acetal, 6α-fluoro-11β,16α,17α,21,21-pentahydroxypregna-1,4-diene-3,20-dione-16,17-acetonide-21,21-(1,2-hexylene) acetal, 6α,9α-difluoro-11β,16α,17α,21,21-pentahydroxypregn-4-ene-3,20-dione-16,17-acetonide-21,21-(21,21-propylene) acetal, 6α-fluoro-11β,16α,17α,21,21-pentahydroxypregn-4-ene-3,20-dione-16,17-acetonide-21,21-(1,2-butylene) acetal, 9α,11β-dichloro-6α-fluoro-16α,17α,21,21-tetrahydroxypregna-1,4-diene-3,20-dione-16,17-acetonide-21,21-(1,2-propylene) acetal, 9α,11β-dichloro-6α-fluoro-16α,17α,21,21-tetrahydroxypregna-1,4-diene-3,20-dione-16,17-acetonide-21,21-(1,2-butylene) acetal, 9α,11β-dichloro-6α-fluoro-16α,17α,21,21-tetrahydroxypregna-1,4-diene-3,20-dione-16,17-acetonide-21,21-(1,2-pentylene) acetal, 9α,11β-dichloro-6α-fluoro-16α,17α,21,21-tetrahydroxypregna-1,4-diene-3,20-dione-16,17-acetonide-21,21-(3-methyl-1,2-butylene) acetal, 9α,11β-dichloro-6α-fluoro-16α,17α,21,21-tetrahydroxypregna-1,4-diene-3,20-dione-16,17-acetonide-21,21(1,2-hexylene) acetal, 9α-chloro-6α-fluoro-11β,16α,17α,21,21-pentahydroxypregna-1,4-diene-3,20-dione-16,17-acetonide-21,21-(1,2-propylene) acetal, 9α-fluoro-11β,16α,17α,21,21-pentahydroxypregna-1,4-diene-3,20-dione-16,17-acetonide-21,21-(1,2-butylene) acetal, 11β,16α,17α,21,21-pentahydroxypregn-4-ene-3,20-dione-16,17-acetonide-21,21-(1,2-pentylene) acetal, 11β,16α,17α,21,21-pentahydroxypregna-1,4-diene-3,20-dione-16,17-acetonide-21,21-(3-methyl-1,2-butylene) acetal, 6α-chloro-11β,16α,17α,21,21-pentahydroxypregna-1,4-diene-3,20-dione-16,17-acetonide-21,21-(1,2-hexylene) acetal, 6α,9α-difluoro-11β,16α,17α,21,21-pentahydroxypregna-1,4-diene-3,20-dione-16,17-acetonide-21,21-(2,3-butylene) acetal, 6α,9α-difluoro-11β,16α,17α,21,21-pentahydroxypregna-1,4-diene-3,20-dione-16,17-acetonide-21,21(4,5-octylene) acetal, 6α,9α-difluoro-11β,16α,17α,21,21-pentahydroxypregna-1,4-diene-3,20-dione-16,17-acetonide-21,21-(2,5-dimethyl-3,4-hexylene) acetal, 6α,9α-difluoro-11β,16α17α,21,21,-pentahydroxypregna-1,4-diene-3,20-dione-16,17-acetonide-21,21-(5,6-decylene) acetal, 6α,9α-difluoro-11β,16α,17α,21,21-pentahydroxypregna-1,4-diene-3,20-dione-16,17-acetonide-21,21-(2,3-pentylene) acetal, 6α,9α-difluoro-11β,16α,17α,21,21-pentahydroxypregna-1,4-diene-3,20-dione-16,17-acetonide-21,21-(4-methyl-2,3-pentylene) acetal, 6α-fluoro-11β,16α,17α,21,21-pentahydroxypregna-1,4-diene-3,20-dione-16,17-acetonide-21,21-(2,3-butylene) acetal, 6α-fluoro-11β,16α,17α,21,21-penytahydroxypregna-1,4-diene-3,20-dione-16,17-acetonide-21,21-(4,5-octylene) acetal, 6α-fluoro-11β,16α,17α,21,21-pentahydroxypregna-1,4-diene-3,20-dione-16,17-acetonide-21,21-(2,5-dimethyl-3,4-hexylene)acetal, 6α-fluoro-11β,16α,17α,21,21-pentahydroxypregna-1,4-diene-3,20-dione-16,17-acetonide-21,21-(5,6-decylene)acetal, 6α-fluoro-11β,16α,17α,21,21-pentahydroxypregna-1,4-diene-3,20-dione-16,17-acetonide-21,21-(2,3-pentylene)acetal, 6α-fluoro-11β,16α,17α,21,21-pentahydroxypregna-1,4-diene-3,20-dione-16,17-acetonide-21,21-(4-methyl-2,3-pentylene)acetal, 6α,9α-difluoro-11β,16α,17α,21,21-pentahydroxypregn-4-ene-3,20-dione-16,17-acetonide-21,21-(2,3-butylene)acetal, 6α-fluoro-11β,16α,17α,21,21-pentahydroxypregn-4-ene-3,20-dione-16,17-acetonide-21,21-(4,5-octylene)acetal, 9α,11β-dichloro-6α-fluoro-16α,17α,21,21-tetrahydroxypregna-1,4-diene-3,20-dione-16,17-acetonide-21,21-(2,3-butylene)acetal, 9α,11β-dichloro-6α-fluoro-16α,17α,21,21-tetrahydroxypregna-1,4-diene-3,20-dione-16,17-acetonide-21,21-(4,5-octylene)acetal, 9α,11β-dichloro-6α-fluoro-16α,17α,21,21-tetrahydroxypregna-1,4-diene-3,20-dione-16,17-acetonide-21,21-(2,5-dimethyl-3,4-hexylene)acetal, 9α,11β-dichloro-6α-fluoro-16α,17α,21,21-tetrahydroxypregna-1,4-diene-3,20-dione-16,17-acetonide-21,21-(5,6-decylene)acetal, 9α,11β-dichloro-6α-fluoro-16α,17α,21,21-tetrahydroxypregna-1,4-diene-3,20-dione-16,17-acetonide-21,21-(2,3-pentylene)acetal, 9α,1162-dichloro-6α-fluoro-16α,17α,21,21-tetetrahydroxypregna-1,4-diene-3,20-dione-16,17-acetonide-21,21-(4-methyl-2,3-pentylene)acetal, 9α-chloro-6α-fluoro-11β,16α,17α,21,21-pentahydroxypregna-1,4-diene-3,20-dione-16,17-acetonide-21,21-(2,5-dimethyl-3,4-hexylene)acetal, 9α-fluoro-11β,16α,17α,21,21-pentahydroxypregna-1,4-diene-3,20-dione-16,17-acetonide-21,21-(5,6-decylene)acetal, 11β,16α,17α,21,21-pentahydroxypregn-4-ene-3,20-dione-16,17-acetonide-21,21-(2,3-pentylene)acetal, 11β,16α,17α,21,21-pentahydroxypregna-1,4-diene-3,20-dione-16,17-acetonide-21,21-(4-methyl-2,3-pentylene)acetal, 6α-chloro-11β,16α,17α,21,21-pentahydroxypregna-1,4-diene-3,20-dione-16,17-acetonide-21,21-(2,3-butylene)acetal, 6α,9α-difluoro-11β,16α,17α,21,21-pentahydroxypregna-1,4-diene-3,20-dione-16,17-acetonide-21,21-(cis-1,2-cyclopentylene)acetal, 6α,9α-difluoro-11β,16α,17α,21,21-pentahydroxypregna-1,4-diene-3,20-dione-16,17-acetonide-21,21-(cis-1,2-cyclohexylene)acetal, 6α-fluoro-11β,16α,17α,21,21-pentahydroxypregna-1,4-diene-3,20-dione-16,17-acetonide-21,21-(cis-1,2-cyclopentylene)acetal, 6α-fluoro-11β,16α,17α,21,21-pentahydroxypregna-1,4-diene-3,20-dione-16,17-acetonide-21,21-(cis-1,2-cyclohexylene)acetal, 6α,9α-difluoro-11β,16α,17α,21,21-pentahydroxypregn-4-ene-3,20-dione-16,17-acetonide-21,21-(cis-1,2-cyclopentylene)acetal, 6α-fluoro-11β,16α,17α,21,21-pentahydroxypregn-4-ene-3,20-dione-16,17-acetonide-21,21-(cis-1,2-cyclohexylene)acetal, 9α,11β-dichloro-6α-fluoro-16α,17α,21,21-tetrahydroxypregna-1,4-diene-3,20-dione-16,17-acetonide-21,21-(cis-1,2-cyclopentylene)acetal, 9α,11β-dichloro-6α-fluoro-16α,17α,21,21-tetrahydroxypregna-1,4-diene-3,20-dione-16,17-acetonide-21,21-(cis-1,2-cyclohexylene)acetal, 9α-chloro-6α-fluoro-11β,16α,17α,21,21-pentahydroxypregna-1,4-diene-3,20-dione-16,17-acetonide-21,21-(cis-1,2-cyclopentylene)acetal, 9α-fluoro-11β,16α,17α,21,21-pentahydroxypregna-1,4-diene-3,20-dione-16,17-acetonide-21,21-(cis-1,2-cyclohexylene)acetal, 11β,16α,17α,21,21pentahydroxypregn-4-ene-3,20-dione-16,17-acetonide-21,21-(cis-1,2-cyclopentylene)acetal, 11β,16α,17α,21,21-pentahydroxypregna-1,4-diene-3,20-dione -16,17-acetonide-21,21-(cis-1,2-cyclohexylene)acetal, 6α-chloro-11β,16α,17α,21,21-pentahydroxypregna-1,4-diene-3,20-dione-16,17-acetonide-21,21-(cis-1,2-cyclopentylene)acetal, 6α,9α-difluoro-11β,16α,17α,21,21-pentahydroxypregna-1,4-diene-3,20-dione-16,17-acetonide-21,21-(1,3-propylene)acetal, 6α-fluoro-11β,16α,17α,21,21-pentahydroxypregna-1,4-diene-3,20-dione-16,17-acetonide-21,21-(1,3-propylene)acetal, 6α,9αdifluoro-11β,16α,17α,21,21-pentahydroxypregn-4-ene-3,20-dione-16,17-acetonide-21,21-(1,3-propylene)acetal, 6α-fluoro-11β,16α,17α,21,21-pentahydroxypregn-4-ene-3,20-dione-16,17-acetonide-21,21-(1,3-propylene)acetal, 9α,11β-dichloro-6α-fluoro-16α,17α,21,21-tetrahydroxypregna-1,4-diene-3,20-dione-16,17-acetonide-21,21-(1,3-propylene)acetal, 9α-chloro-6α-fluoro-11β,16α,17α,21,21-pentahydroxypregna-1,4-diene-3,20-dione-16,17-acetonide-21,21-(1,3-propylene)acetal, 9α-fluoro-11β,16α,17α,21,21-pentahydroxypregna-1,4-diene-3,20-dione-16,17-acetonide-21,21-(1,3-propylene)acetal, 11β,16α,17α,21,21-pentahydroxypregn-4-ene-3,20-dione-16,17-acetonide-21,21-(1,3-propylene)acetal, 11β,16α,17α,21,21-pentahydroxypregna-1,4-diene-3,20-dione-16,17-acetonide-21,21-(1,3-propylene)acetal, 6α-chloro-11β,16α,17α,21,21-pentahydroxypregna-1,4-diene-3,20-dione-16,17-acetonide-21,21-(1,3-propylene)acetal, 6α,9α-difluoro-11β,16α,17α,21,21-pentahydroxypregna-1,4-diene-3,20-dione-16,17-acetonide-21,21-(1,3-butylene)acetal, 6α,9α-difluoro-11β,16α,17α,21,21-pentahydroxypregna-1,4-diene-3,20-dione-16,17-acetonide-21,21-(1,3-pentylene)acetal, 6α,9α-difluoro-11β,16α,17α,21,21-pentahydroxypregna-1,4-diene-3,20-dione-16,17-acetonide-21,21-(1,3hexylene)acetal, 6α,9α-difluoro-11β,16α,17α,21,21-pentahydroxypregna-1,4-diene-3,20-dione-16,17-acetonide-21,21-(1,3-heptylene)acetal, 6α,9α-difluoro-11β,16α,17α,21,21-pentahydroxypregna-1,4-diene-3,20-dione-16,17-acetonide-21,21-(2-methyl-1,3-propylene)acetal, 6α,9α-difluoro-11β,16α,17α,21,21-pentahydroxypregna-1,4-diene-3,20-dione-16,17-acetonide-21,21-(2-ethyl-1,3-propylene)acetyl, 6α,9α-difluoro-11β,16α,17α,21,21-pentahydroxypregna-1,4-diene-3,20-dione-16,17-acetonide-21,21-(2-n-propyl-1,3-propylene)acetal, 6α,9α-difluoro-11β,16α,17α,21,21-pentahydroxypregna-1,4-diene-3,20-dione-16,17-acetonide-21,21-(2-n-butyl-1,3-propylene)acetal, 6α-fluoro-11β,16α,17α,21,21-pentahydroxypregna-1,4-diene-3,20-dione-16,17-acetonide-21,21-(1,3-butylene)acetal, 6α-fluoro-11β,16α,17α,21,21-pentahydroxypregna-1,4-diene-3,20-dione-16,17-acetonide-21,21-(1,3-pentylene)acetal, 6α-fluoro-11β,16α,17α,21,21-pentahydroxypregna-1,4-diene-3,20-dione-16,17-acetonide-21,21-(1,3-hexylene)acetal, 6α-fluoro-11β,16α,17α,21,21-penyahydroxypregna-1,4-diene-3,20-dione-16,17-acetonide-21,21-(1,3-heptylene)acetal, 6α-fluoro-11β,16α,17α,21,21-pentahydroxypregna-1,4-diene-3,20-dione-16,17-acetonide-21,21-(2-methyl-1,3-propylene)acetal, 6α-fluoro-11β,16α,17α,21,21-pentahydroxypregna-1,4-diene-3,20-dione-16,17-acetonide-21,21-(2-ethyl-1,3-propylene)acetal, 6α-fluoro-11β,16α,17α,21,21-pentahydroxypregna-1,4diene-3,20-dione-16,17-acetonide-21,21-(2-n-propyl-1,3-propylene)acetal, 6α-fluoro-11β,16α,17α,21,21-pentahydroxypregna-1,4-diene-3,20-dione-16,17-acetonide-21,21-(2-n-butyl-1,3-propylene)acetal, 6α,9α-difluoro-11β,16α,17α,21,21-pentahydroxypregn-4-ene-3,20-dione-16,17-acetonide-21,21-(1,3-butylene)acetal, 6α-fluoro-11β,16α,17α,21,21-pentahydroxypregn-4-ene-3,20-dione-16,17-acetonide-21,21-(1,3-pentylene)acetal, 9α,11β-dichloro-6α-fluoro-16α,17α,21,21-tetrahydroxypregna-1,4-diene-3,20-dione-16,17-acetonide-21,21-(1,3-butylene)acetal, 9α,11β-dichloro-6α,17α, 21,21-tetrahydroxypregna-1,4-diene-3,20-dione-16,17-acetonide-21,21-(1,3-pentylene)acetal, 9α,11β-dichloro-6α-fluoro-16α,17α,21,21-tetrahydroxypregna-1,4-diene-3,20-dione-16,17-acetonide-21,21-(1,3-hexylene)acetal, 9α,11β-dichloro-6α-fluoro-16α,17α,21,21-tetrahydroxypregna-1,4-diene-3,20-dione-16,17-acetonide-21,21-(1,3-heptylene)acetal, 9α,11β-dichloro-6α-fluoro-16α,17α,21,21-tetrahydroxypregna-1,4-diene-3,20-dione-16,17-acetonide-21,21-(2-methyl-1,3-propylene)acetal, 9α,11β-dichloro-6α-fluoro-16α,17α,21,21-tetrahydroxypregna-1,4-diene-3,20-dione-16,17-acetonide-21,21-(2-ethyl-1,3-propylene)acetal, 9α,11β-dichloro-6α-fluoro-16α,17α,21,21 -tetrahydroxypregna-1,4-diene-3,20-dione-16,17-acetonide-21,21-(2-n-propyl-1,3-propylene)acetal, 9α,11β-dichloro-6α-fluoro-16α,17α,21,21-tetrahydroxypregna-1,4-diene-3,20-dione-16,17-acetonide-21,21-(2-n-butyl-1,3-propylene)acetal, 9α-chloro-6α-fluoro-11β,16α,17α,21,21-pentahydroxypregna-1,4-diene-3,20-dione-16,17-acetonide-21,21-(1,3-hexylene)acetal, 9α-fluoro-11β,16α,17α,21,21-pentahydroxypregna-1,4-diene-3,20-dione-16,17acetonide-21,21-(1,3-heptylene)acetal, 11β,16α,17α,21,21-pentahydroxypregn-4-ene-3,20-dione-16, 17-acetonide-21,21-(2-methyl-1,3-propylene)acetal, 11β,16α,17α,21,21-pentahydroxypregna-1,4-diene-3,20-dione-16,17-acetonide-21,21-(2-ethyl-1,3-propylene)acetal, 6α-chloro-11β,16α,17α,21,21-pentahydroxypregna-1,4-diene-3,20-dione-16,17-acetonide-21,21-(2-isopropyl-1,3-propylene) acetal, 6α,9α-diffluoro-11β,16α,17α,21,21-pentahydroxypregna-1,4-diene-3,20-dione-16,17-acetonide-21,21-(2,2,-dimethyl-1,3-propylene)acetal, 6α,9α-difluoro-11β,16α,17α,21,21-pentahydroxypregna-1,4-diene-3,20-dione-16,17-acetonide-21,21-(2,2-diisopropyl-1,3-propylene)acetal, 6α,9α-difluoro-11β,16α,17α,21,21-pentahydroxypregna-1,4-diene-3,20-dione-16,17-acetonide-21,21-(2-methyl-2-n-propyl-1,3-propylene)acetal, 6α,9α-difluoro-11β,16α,17α,21,21-pentahydroxypregna-1,4-diene-3,20-dione-16,17-acetonide-21,21-(2-ethyl-2-n-butyl-1,3-propylene)acetal, 6α,9α-difluoro-11β,16α,17α,21,21-pentahydroxypregna-1,4-diene-3,20-dione-16,17-acetonide-21,21-(2-methyl-1,3-butylene) acetal, 6α,9α-difluoro-11β,16α,17α,21,21-pentahydroxypregna-1,4-diene-3,20-dione-16,17-acetonide-21,21-(2,4-hexylene)acetal, 6α,9α-difluoro-11β,16α,17α,21,21-pentahydroxypregna-1,4-diene-3,20-dione-16,17-acetonide-21,21-(4,6-nonylene)acetal, 6α-fluoro-11β,16α,17α,21,21-pentahydroxypregna-1,4-diene-3,20-dione-16,17-acetonide-21,21-(2,2-diethyl-1,3-propylene) acetal, 6α-fluoro-11β,16α,17α,21,21-pentahydroxypregna-1,4-diene-3,20-dione-16,17-acetonide-21,21-(2-methyl-2-isopropyl-1,3-propylene)acetal, 6α-fluoro-11β,16α,17α,21,21-pentahydroxypregna-1,4-diene-3,20-dione-16,17-acetonide-21,21-(2-methyl-1,3-butylene)acetal, 6α-fluoro-11β,16α,17α,21,21-pentahydroxypregna-1,4-diene-3,20-dione-16,17-acetonide-21,21-(2,4-pentylene)acetal, 6α-fluoro-11β,16α,17α,21,21-pentahydroxypregna-1,4-diene-3,20-dione-16,17-acetonide-21,21-(4,6-nonylene)acetal, 6α,9α-difluoro-11β,16α,17α,21,21-pentahydroxypregna-4-ene-3,20-dione-16,17-acetonide-21,21-(2,2-dimethyl-1,3-propylene)acetal, 6α-fluoro-11β,16α,17α,21,21-pentahydroxypregna-4-ene-3,20-dione-16,17-acetonide-21,21-(2-methyl-2-isopropyl-1,3-propylene)acetal, 9α,11β-dichloro-6α-fluoro-16α,17α,21,21-tetrahydroxypregna-1,4-diene-3,20-dione-16,17-acetonide-21,21-(2,2-dimethyl-1,3-propylene)acetal, 9α,11β-dichloro-6α-fluoro-16α,17α,21,21-tetrahydroxypregna-1,4-diene-3,20-dione-16,17-acetonide-21,21(2,2-diisopropyl-1,3-propylene)acetal, 9α,11β-dichloro-6α-fluoro-16α,17α,21,21-tetrahydroxypregna-1,4-diene-3,20-dione-16,17-acetonide-21,21-(2-ethyl-2-n-butyl-1,3-propylene)acetal, 9α,11β-dichloro-6α-fluoro-16α,17α,21,21-tetrahydroxypregna-1,4-diene-3,20-dione-16,17-acetonide-21,21-(2-methyl-1,3-butylene)acetal, 9α,11β-dichloro-6α-fluoro-16α,17α,21,21-tetrahydroxypregna-1,4-diene-3,20-dione-16,17-acetonide-21,21-(2,4-hexylene)acetal, 9α,11β-dichloro-6α-fluoro-16α,17α,21,21-tetrahydroxypregna-1,4-diene-3,20-dione-16,17-acetonide-21,21-(4,6-nonylene)acetal, 9α-chloro-6α-fluoro-11β,16α,17α,21,21-pentahydroxypregna-1,4-diene-3,20-dione-16,17-acetonide-21,21-(2,2-diethyl-1,3-propylene)acetal, 9α-fluoro-11β,16α,17α,21,21-pentahydroxypregna-1,4-diene-3,20-dione-16,17-acetonide-21,21-(2-ethyl-2-isopropyl-1,3-propylene)acetal, 11β,16α,17α,21,21-pentahydroxypregna-4-ene-3,20-dione-16, 17-acetonide-21,21-(2-methyl-1,3-butylene)acetal, 11β,16α,17α,21,21-pentahydroxypregna-1,4-diene-3,20-dione, 16,17-acetonide-21,21-(2,4-pentylene)acetal, and 6α-chloro-11β,16α,17α,21,21-pentahydroxypregna-1,4-diene-3,20-dione-16,17-acetonide-21,21-(4,6-nonylene)acetal.

EXAMPLE 4

This example illustrates steps 2 and 3 of the second precess described for preparing the compounds of the invention.

In this example, 250 mg. of 6α,9α-difluoro-11β,16α,-17α, 21,21-pentahydroxypregna-1,4-diene-3,20-dione-16,17-acetonide is heated under high vacuum is an oil bath at 110° C for 30 minutes. Thereafter, the product is cooled to room temperature and a solution of 2,2-dimethyl-1,3-propanediol in 2 ml. of methylene chloride is added. The mixture is then stirred at room temperature for 3 hours. Thereafter, 0.5 ml. of triethylamine is added, the mixture is cooled to −20° C, and then 0.10 ml. of methanesulfonyl chloride is added and the reaction mixture is allowed to warm to room temperature. The mixture is then washed with water, dried over sodium sulfate and evaporated to dryness. The residue is chromatographed on silica gel. Elution with 12% acetone in benzene yields 80 mg. 6α,9α-difluoro-11β,16α,17α,21,21-pentahydroxypregna-1,4-diene-3,20-dione-16,17-acetonide-21,21-(2,2-dimethyl-1,3-propylene)acetal.

EXAMPLE 5

Following the procedure of Example 4, using equivalent amounts of appropriate starting materials enumerated in Table 3 (see Example 3) and Table 6, hereinbelow, is productive of the corresponding steroidal 21-cyclic acetals enumerated in Table 7.

TABLE 6

$$HO-\underset{R^2}{\overset{R^1}{C}}-\left[\underset{R^4}{\overset{R^3}{C}}\right]_n-\underset{R^6}{\overset{R^5}{C}}-OH$$

(C)

| n | $R^1/R^2$ | $R^3/R^4$ | $R^5/R^6$ |
|---|---|---|---|
| 0 | H/H | | H/H |
| 0 | $C_1$/H | | H/H |
| 0 | $C_2$/H | | H/H |
| 0 | $C_3{}^n$/H | | H/H |
| 0 | $C_3{}^i$/H | | H/H |
| 0 | $C_4{}^n$/H | | H/H |
| 0 | $C_4{}^i$/H | | H/H |
| 0 | $C_4{}^{sec}$/H | | H/H |
| 0 | $C_1$/H | | $C_1$/H |
| 0 | $C_1$/H | | $C_2$/H |
| 0 | $C_1$/H | | $C_3{}^n$/H |

TABLE 6-continued $$HO-\underset{R^2}{\overset{R^1}{\underset{|}{C}}}-\left[\underset{R^4}{\overset{R^3}{\underset{|}{C}}}\right]_n-\underset{R^6}{\overset{R^5}{\underset{|}{C}}}-OH$$

(C)

| n | $R^1/R^2$ | $R^3/R^4$ | $R^5/R^6$ |
|---|---|---|---|
| 0 | $C_1$/H | | $C_3^i$/H |
| 0 | $C_1$/H | | $C_4^n$/H |
| 0 | $C_2$/H | | $C_2$/H |
| 0 | $C_2$/H | | $C_4^n$/H |
| 0 | $C_3^n$/H | | $C_3^n$/H |
| 0 | $C_3^i$/H | | $C_3^i$/H |
| 0 | $C_4^n$/H | | $C_4^n$/H |
| 0 | $(CH_2)_3$/H | | seeR$^1$/H |
| 0 | $(CH_2)_4$/H | | seeR$^1$/H |
| 1 | $C_1$/H | H/H | H/H |
| 1 | $C_2$H | H/H | H/H |
| 1 | $C_3^n$/H | H/H | H/H |
| 1 | $C_3^i$/H | H/H | H/H |
| 1 | $C_4^n$/H | H/H | H/H |
| 1 | H/H | $C_1$/H | H/H |
| 1 | H/H | $C_2$/H | H/H |
| 1 | H/H | $C_3^n$/H | H/H |
| 1 | H/H | $C_3^i$/H | H/H |
| 1 | H/H | $C_4^n$/H | H/H |
| 1 | H/H | $C_4^i$/H | H/H |
| 1 | H/H | $C_4^{sec}$/H | H/H |
| 1 | H/H | $C_4^t$/H | H/H |
| 1 | H/H | $C_1/C_1$ | H/H |
| 1 | H/H | $C_1/C_2$ | H/H |
| 1 | H/H | $C_1/C_3^n$ | H/H |
| 1 | H/H | $C_1/C_3^i$ | H/H |
| 1 | H/H | $C_1/C_4^n$ | H/H |
| 1 | H/H | $C_1/C_4^i$ | H/H |
| 1 | H/H | $C_1/C_4^{sec}$ | H/H |
| 1 | H/H | $C_1/C_4^t$ | H/H |
| 1 | H/H | $C_2/C_2$ | H/H |
| 1 | H/H | $C_2/C_3^n$ | H/H |
| 1 | H/H | $C_2/C_3^i$ | H/H |
| 1 | H/H | $C_2/C_4^n$ | H/H |
| 1 | H/H | $C_2/C_4^i$ | H/H |
| 1 | H/H | $C_2/C_4^{sec}$ | H/H |
| 1 | H/H | $C_3^n/C_3^n$ | H/H |
| 1 | H/H | $C_3^i/C_3^i$ | H/H |
| 1 | H/H | $C_4^n/C_4^n$ | H/H |
| 1 | H/H | $C_4^i/C_4^i$ | H/H |
| 1 | $C_1$/H | $C_1$/H | H/H |
| 1 | $C_1$/H | $C_2$/H | H/H |
| 1 | $C_1$/H | $C_3^n$/H | H/H |
| 1 | $C_1$/H | $C_3^i$/H | H/H |
| 1 | $C_2$/H | $C_1$/H | H/H |
| 1 | $C_3^i$/H | $C_1$/H | H/H |
| 1 | $C_3^n$/H | $C_2$/H | H/H |
| 1 | $C_3^n$/H | $C_3^n$/H | H/H |
| 1 | $C_4^n$/H | $C_2$/H | H/H |
| 1 | $C_4^n$/H | $C_3^n$/H | H/H |
| 1 | $C_1$/H | H/H | $C_1$/H |
| 1 | $C_1$/H | H/H | $C_2$/H |
| 1 | $C_1$/H | H/H | $C_3^n$/H |
| 1 | $C_1$/H | H/H | $C_3^i$/H |
| 1 | $C_2$/H | H/H | $C_3^n$/H |
| 1 | $C_3^n$/H | H/H | $C_3^n$/H |
| 1 | $C_3^i$/H | H/H | $C_3^i$/H |
| 1 | $C_3^n$/H | H/H | $C_4^n$/H |
| 1 | $C_3^i$/H | H/H | $C_4^n$/H |
| 1 | H/H | $C_1/C_1$ | $C_1$/H |
| 1 | H/H | $C_1/C_1$ | $C_2$/H |
| 1 | H/H | $C_1/C_1$ | $C_3^n$/H |
| 1 | H/H | $C_1/C_1$ | $C_3^i$/H |
| 1 | H/H | $C_1/C_1$ | $C_4^n$/H |
| 1 | H/H | $C_1/C_1$ | $C_4^i$/H |
| 1 | H/H | $C_2/C_4^n$ | $C_1$/H |
| 1 | $C_1$/H | $C_1$/H | $C_1$/H |
| 1 | $C_1$/H | $C_1$/H | $C_3^n$/H |
| 1 | $C_2$/H | $C_3^n$/H | $C_2$/H |
| 1 | $C_3^n$/H | $C_2$/H | $C_3^n$/H |
| 1 | $C_3^n$/H | $C_2$/H | $C_3^i$/H |
| 1 | $C_3^n$/H | $C_2$/H | $C_4^n$/H |
| 1 | $C_1$/H | $C_1/C_1$ | $C_1$/H |
| 1 | $C_1$/H | $C_1/C_1$ | $C_2$/H |
| 1 | $C_1$/H | $C_1/C_1$ | $C_3^i$/H |
| 1 | $C_1$/H | $C_1/C_1$ | $C_1$/H |
| 1 | $C_2$/H | $C_1/C_1$ | $C_3^i$/H |
| 1 | $C_3^i$/H | $C_1/C_1$ | $C_4^n$/H |

Note - $C_1$ = methyl; $C_2$ = ethyl; $C_3^n$ = n-propyl; $C_3^i$ = isopropyl; $C_4^n$ = n-butyl; $C_4^{sec}$ = sec-butyl; $C_4^i$ = isobutyl; $C_4^t$ = tert-butyl.

TABLE 7

6α,9α-difluoro-11β,16α,17α,21,21-pentahydroxy-pregna-1,4-diene-3,20-dione-16,17-acetonide-21,21-(4-methyl-1,2-pentylene) acetal, 6α,9α-difluoro-11β,16α,17α,21,21-pentahydroxy-pregna-1,4-diene-3,20-dione-16,17-acetonide-21,21-(3-methyl-1,2-pentylene) acetal, 6α-fluoro-11β,16α,17α,21,21-pentahydroxypregna-1,4-diene-3,20-dione-16,17-acetonide-21,21-(4-methyl-1,2-pentylene) acetal, 6α-fluoro-11β,16α,17α,21,21-pentahydroxypregna-1,4-diene-3,20-dione-16,17-acetonide-21,21-(3-methyl-1,2-pentylene) acetal, 6α,9α-difluoro-11β,16α,17α,21,21-pentahydroxy-pregn-4-ene-3,20-dione-16,17-acetonide-21,21-(4-methyl-1,2-pentylene) acetal, 6αfluoro-11β,16α,17α,21,21-pentahydroxypregn-4-ene-3,20-dione-16,17-acetonide-21,21-(3-methyl-1,2-pentylene)acetal, 9α,11β-dichloro-6α-fluoro-16α,17α,21,21-tetrahydroxypregna-1,4-diene-3,20-dione-16,17-acetonide-21,21-(4-methyl-1,2-pentylene)acetal, 9α,11β-dichloro-6α-fluoro-16α,17α,21,21-tetrahydroxypregna-1,4-diene-3,20-dione-16,17-acetonide-21,21-(3-methyl-1,2-pentylene)acetal, 9α-chloro-6α-fluoro-11β,16α,17α,21,21-pentahydroxypregna-1,4-diene-3,20-dione-16,17-acetonide-21,21-(4-methyl-1,2-pentylene)acetal, 9α-fluoro-11β,16α,17α,21,21-pentahydroxypregna-1,4-diene-3,20-dione-16,17-acetonide-21,21-(3-methyl-1,2-pentylene)acetal, 11β,16α,17α,21,21-pentahydroxypregn-4-ene-3,20-dione-16,17-acetonide-21,21-(4-methyl-1,2-pentylene)acetal, 11β,16α,17α,21,21-pentahydroxypregna-1,4-diene-3,20-dione-16,17-acetonide-21,21-(3-methyl-1,2-pentylene)acetal, 6α-chloro-11β,16α,17α,21,21-pentahydroxypregna-1,4-diene-3,20-dione-16,17-acetonide-21,21-(4-methyl-1,2-pentylene)acetal, 6α,9α-difluoro-11β,16α,17α,21,21-pentahydroxy-pregna-1,4-diene-3,20-dione-16,17-acetonide-21,21-(2,3-hexylene)acetal, 6α,9α-difluoro-11β,16α,17α,21,21-pentahydroxy-pregna-1,4-diene-3,20-dione-16,17-acetonide-21,21-(2,3-heptylene)acetal, 6α,9α-difluoro-11β,16α,17α,21,21-pentahydroxy-pregna-1,4-diene-3,20-dione-16,17-acetonide-21,21-(3,4-hexylene)acetal, 6α,9α-difluoro-11β,16α,17α,21,21-pentahydroxy-pregna-1,4-diene-3,20-dione-16,17-acetonide-21,21-(6-methyl-3,4-heptylene)acetal, 6α-fluoro-11β,16α,17α,21,21-pentahydroxypregna-1,4-diene-3,20-dione-16,17-acetonide-21,21-(2,3-hexylene)acetal, 6α-fluoro-11β,16α,17α,21,21-pentahydroxypregna-1,4-diene-3,20-dione-16,17-acetonide-21,21-(2,3-heptylene)acetal, 6α-fluoro-11β,16α,17α,21,21-pentahydroxypregna-1,4-diene-3,20-dione-16,17-acetonide-21,21-(3,4-hexylene)acetal, 6α-fluoro-11β,16α,17α,21,21-pentahydroxypregna-1,4-diene-3,20-dione-16,17-acetonide-21,21-(6-methyl-3,4-heptylene)acetal, 6α,9α-difluoro-11β,16α,17α,21,21-pentahydroxy-pregn-4-ene-3,20-dione-16,17-acetonide-21,21-(2,3-hexylene)acetal, 6α-fluoro-11β,16α,17α,21,21-pentahydroxypregn-4-ene-3,20-dione-16,17-acetonide-21,21-(2,3-heptylene)acetal, 9α,11β-dichloro-6α-fluoro-16α,17α,21,21-tetrahydroxypregna-1,4-diene-3,20-dione-16,17-acetonide-21,21-(2,3-hexylene)acetal, 9α,11β-dichloro-6α-fluoro-16α,17α,21,21-tetrahydroxypregna-1,4-diene-3,20-dione-16,17-acetonide-21,21-(2,3-heptylene)acetal, 9α,11β-dichloro-6α-fluoro-16α,17α,21,21-tetrahydroxypregna-1,4-diene-3,20-dione-16,17-acetonide-21,21-(3,4-hexylene)acetal, 9α,11β-dichloro-6α-fluoro-16α,17α,21,21-tetrahydroxypregna-1,4-diene-3,20-dione-16,17-acetonide-21,21-(6-methyl-3,4-heptylene)acetal, 9α-chloro-6α-fluoro-11β,16α,17α,21,21-pentahydroxypregna-1,4-diene-3,20-dione-16,17-acetonide-21,21-(2,3-hexylene)acetal, 9α-fluoro-11β,16α,17α,21,21-pentahydroxypregna-1,4-diene-3,20-dione-16,17-acetonide-21,21-(2,3-heptylene)acetal, 11β,16α,17α,21,21-pentahydroxypregn-4-ene-3,20-dione-16,17-acetonide-21,21-(3,4-hexylene)acetal, 11β,16α,17α,21,21-pentahydroxypregna-1,4-diene-3,20-dione-16,17-acetonide-21,21-(6-methyl-3,4-heptylene)acetal, 6α-chloro-11β,16α,17α,21,21-pentahydroxypregna-1,4-diene-3,20-dione-16,17-acetonide-21,21-(2,3-hexylene)acetal, 6α,9α-difluoro-11β,16α,17α,21,21-pentahydroxypregna-1,4-diene-3,20-dione-16,17-acetonide-21,21-(4-methyl-1,3-pentylene)acetal, 6α,9α-difluoro-11β,16α,17α,21,21-pentahydroxypregna-1,4-diene-3,20-dione-16,17-acetonide-21,21-(2-isobutyl-1,3-propylene)acetal, 6α-fluoro-11β,16α,17α,21,21-pentahydroxypregna-1,4-diene-3,20-dione-16,17-acetonide-21,21-(4-methyl-1,3-pentylene)acetal, 6α-fluoro-11β,16α,17α,21,21-pentahydroxypregna-1,4-diene-3,20-dione-16,17-acetonide-21,21-(2-sec-butyl-1,3-propylene)acetal, 6α,9α-difluoro-11β,16α,17α,21,21-pentahydroxypregn-4-ene-3,20-dione-16,17-acetonide-21,21-(4-methyl-1,3-pentylene)acetal, 6α-fluoro-11β,16α,17α,21,21-pentahydroxypregn-4-ene-3,20-dione-16,17-acetonide-21,21-(2-isobutyl-1,3-propylene)acetal, 9α,11β-dichloro-6α-fluoro-16α,17α,21,21-tetrahydroxypregna-1,4-diene-3,20-dione-16,17-acetonide-21,21-(4-methyl-1,3-pentylene)acetal, 9α,11β-dichloro-6α-fluoro-16α,17α,21,21-tetrahydroxypregna-1,4-diene-3,20-dione-16,17-acetonide-21,21-(2-tert-butyl-1,3-propylene)acetal, 9α-chloro-6α-fluoro-11β,16α,17α,21,21-pentahydroxypregna-1,4-diene-3,20-dione-16,17-acetonide-21,21-(2-isobutyl-1,3-propylene)acetal, 9α-fluoro-11β,16α,17α,21,21-pentahydroxypregna-1,4-diene-3,20-dione-16,17-acetonide-21,21-(2-sec-butyl-1,3-propylene)acetal, 11β,16α,17α,21,21-pentahydroxypregn-4-ene-3,20-dione-16,17-acetonide-21,21-(2-tert-butyl-1,3-propylene)acetal, 11β,16α,17α,21,21-pentahydroxypregna-1,4-diene-3,20-dione-16,17-acetonide-21,21-(4-methyl-1,3-pentylene)acetal, 6α-chloro-11β,16α,17α,21,21-pentahydroxypregna-1,4-diene-3,20-dione-16,17-acetonide-21,21-(2-isobutyl-1,3-propylene)acetal, 6α,9α-difluoro-11β,16α,17α,21,21-pentahydroxypregna-1,4-diene-3,20-dione-16,17-acetonide-21,21-(2-methyl-2-ethyl-1,3-propylene)acetal, 6α,9α-difluoro-11β,16α,17α,21,21-pentahydroxypregna-1,4-diene-3,20-dione-16,17-acetonide-21,21-(2-methyl-2-n-butyl-1,3-propylene)acetal, 6α,9α-difluoro-11β,16α,17α,21,21-pentahydroxypregna-1,4-diene-3,20-dione-16,17-acetonide-21,21-(2-ethyl-2-n-propyl-1,3-propylene)acetal, 6α,9α-difluoro-11β,16α,17α,21,21-pentahydroxypregna-1,4-diene-3,20-dione-16,17-acetonide-21,21-(2-ethyl-2-isobutyl-1,3-propylene)acetal, 6α,9α-difluoro-11β,16α,17α,21,21-pentahydroxypregna-1,4-diene-3,20-dione-16,17-acetonide-21,21-(2,2-di-n-butyl-1,3-propylene)acetal, 6α,9α-difluoro-11β,16α,17α,21,21-pentahydroxypregna-1,4-diene-3,20-dione-16,17-acetonide-21,21-(2-ethyl-1,3-butylene)acetal, 6α,9α-difluoro-11β,16α,17α,21,21-pentahydroxypregna-1,4-diene-3,20-dione-16,17-acetonide-21,21-(2-n-propyl-1,3-butylene)acetal, 6α,9α-difluoro-11β,16α,17α,21,21-pentahydroxypregna-1,4-diene-3,20-dione-16,17-acetonide-21,21-(2-methyl-1,3-pentylene)acetal, 6α,9α-difluoro-11β,16α,17α,21,21-pentahydroxypregna-1,4-diene-3,20-dione-16,17-acetonide-21,21-(2,4-dimethyl-1,3-pentylene)acetal, 6α,9α-difluoro-11β,16α,17α,21,21-pentahydroxypregna-1,4-diene-3,20-dione-16,17-acetonide-21,21-(2-ethyl-1,3-hexylene)acetal, 6α,9α-difluoro-11β,16α,17α,21,21-pentahydroxypregna-1,4-diene-3,20-dione-16,17-acetonide-21,21-(2-n-propyl-1,3-hexylene)acetal, 6α,9α-difluoro-11β,16α,17α,21,21-pentahydroxypregna-1,4-diene-3,20-dione-16,17-acetonide-21,21-(2-ethyl-1,3-heptylene)acetal, 6α,9α-difluoro-11β,16α,17α,21,21-pentahydroxypregna-1,4-diene-3,20-dione-16,17-acetonide-21,21-(2-n-propyl-1,3-heptylene)acetal, 6α,9α-difluoro-11β,16α,17α,21,21-pentahydroxypregna-1,4-diene-3,20-dione-16,17-acetonide-21,21-(2,4-heptylene)actal, 6α,9α-difluoro-11β,16α,17α,21,21-pentahydroxypregna-1,4-diene-3,20-dione-16,17-acetonide-21,21-(5-methyl-2,4-hexylene)acetal, 6α,9α-difluoro-11β,16α,17α,21,21-pentahydroxypregna-1,4-diene-3,20-dione-16,17-acetonide-21,21-(3,5-octylene)acetal, 6α,9α-difluoro-11β,16α,17α,21,21-pentahydroxypregna-1,4-diene-3,20-dione-16,17-acetonide-21,21-(2,6-dimethyl-3,5-heptylene)acetal, 6α,9α-difluoro-11β,16α,17α,21,21-pentahydroxypregna-1,4-diene-3,20-dione-16,17-acetonide-21,21-(4,6-decylene)acetal, 6α-fluoro-11β,16α,17α,21,21-pentahydroxypregna-1,4-diene-3,20-dione-16,17-acetonide-21,21-(2-methyl-2-ethyl-1,3-propylene)acetal, 6α-fluoro-11β,16α,17α,21,21-pentahydroxypregna-1,4-diene-3,20-dione-16,17-acetonide-21,21-(2-methyl-2-isobutyl-1,3-propylene)acetal, 6α-fluoro-11β,16α,17α,21,21-pentahydroxypregna-1,4-diene-3,20-dione-16,17-acetonide-21,21-(2-methyl-2-n-propyl-1,3-propylene)acetal, 6α-fluoro-11β,16α,17α,21,21-pentahydroxypregna-1,4-diene-3,20-dione-16,17-acetonide-21,21-(2-ethyl-2-sec-butyl-1,3-propylene)acetal, 6α-fluoro-11β,16α,17α,21,21-pentahydroxypregna-1,4-diene-3,20-dione-16,17-acetonide-21,21-(2,2-diisobutyl-1,3-propylene)acetal,
6α-fluoro-11β,16α,17α, 21,21-pentahydroxypregna-1,4-diene-3,20-dione-16,17-acetonide-21,21-(2-ethyl-1,3-butylene)acetal,
6α-fluoro-11β,16α,17α,21,21-pentahydroxypregna-1,4-diene-3,20-dione-16,17-acetonide-21,21-(2-isopropyl-1,3-butylene)acetal,
6α-fluoro-11β,16α,17α,21,21-pentahydroxypregna-1,4-diene-3,20-dione-16,17-acetonide-21,21-(2-methyl-1,3-pentylene)acetal,
6α-fluoro-11β,16α,17α,21,21-pentahydroxypregna-1,4-diene-3,20-dione-16,17-acetonide-21,21-(2,4-dimethyl-1,3-pentylene)acetal,
6α-fluoro-11β,16α,17α,21,21-pentahydroxypregna-1,4-diene-3,20-dione-16,17-acetonide-21,21-(2-ethyl-1,3-hexylene)acetal,
6α-fluoro-11β,16α,17α,21,21-pentahydroxypregna-1,4-diene-3,20-dione-16,17-acetonide-21,21-(2-n-propyl-1,3-hexylene)acetal,
6α-fluoro-11β,16α,17α,21,21-pentahydroxypregna-1,4-diene-3,20-dione-16,17-acetonide-21,21-(2-ethyl-1,3-heptylene)acetal,
6α-fluoro-11β,16α,17α,21,21-pentahydroxypregna-1,4-diene-3,20-dione-16,17-acetonide-21,21-(2-n-propyl-1,3-heptylene)acetal,
6α-fluoro-11β,16α,17α,21,21-pentahydroxypregna-1,4-diene-3,20-dione-16,17-acetonide-21,21-(2,4-heptylene)acetal,
6α-fluoro-11β,16α,17α,21,21-pentahydroxypregna-1,4-diene-3,20-dione-16,17-acetonide-21,21-(5-methyl-2,4-hexylene)acetal,
6α-fluoro-11β,16α,17α,21,21-pentahydroxypregna-1,4-diene-3,20-dione-16,17-acetonide-21,21-(3,5-octylene)acetal,
6α-fluoro-11β,16α,17α,21,21-pentahydroxypregna-1,4-diene-3,20-dione-16,17-acetonide-21,21-(2,6-dimethyl-3,5-heptylene)acetyl,
6α-fluoro-11β,16α,17α,21,21-pentahydroxypregna-1,4-diene-3,20-dione-16,17-acetonide-21,21-(2-methyl-3,5-nonylene)acetal,
6α,9α-difluoro-11β,16α,17α,21,21-pentahydroxypregn-4-ene-3,20-dione-16,17-acetonide-21,21-(2-methyl-2-ethyl-1,3-propylene)acetal,
6α-fluoro-11β,16α,17α,21,21-pentahydroxypregn-4-ene-3,20-dione-16,17-acetonide-21,21-(2-methyl-2-n-butyl-1,3-propylene)acetal,
9α,11β-dichloro-6α-fluoro-16α,17α,21,21-tetrahydroxypregna-1,4-diene-3,20-dione-16,17-acetonide-21,21-(2-methyl-2-ethyl-1,3-propylene)acetal,
9α,11β-dichloro-6α-fluoro-16α,17α,21,21-tetrahydroxypregna-1,4-diene-3,20-dione-16,17-acetonide-21,21-(2-methyl-2-secbutyl-1,3-propylene)acetal,
9α,11β-dichloro-6α-fluoro-16α,17α,21,21-tetrahydroxypregna-1,4-diene-3,20-dione-16,17-acetonide-21,21-(2-ethyl-2-n-propyl-1,3-propylene)acetal,
9α,11β-dichloro-6α-fluoro-16α,17α,21,21-tetrahydroxypregna-1,4-diene-3,20-dione-16,17-acetonide-21,21-(2-ethyl-2-isobutyl-1,3-propylene)acetal,
9α,11β-dichloro-6α-fluoro-16α,17α,21,21-tetrahydroxypregna-1,4-diene-3,20-dione-16,17-acetonide-21,21-(2,2-di-n-butyl-1,3-propylene)acetal,
9α,11β-dichloro-6α-fluoro-16α,17α,21,21-tetrahydroxypregna-1,4-diene-3,20-dione-16,17-acetonide-21,21-(2-ethyl-1,3-butylene)acetal,
9α,11β-dichloro-6α-fluoro-16α,17α,21,21-tetrahydroxypregna-1,4-diene-3,20-dione-16,17-acetonide-21,21-(2-n-propyl-1,3-butylene)acetal,
9α,11β-dichloro-6α-fluoro-16α,17α,21,21-tetrahydroxypregna-1,4-diene-3,20-dione-16,17-acetonide-21,21-(2-methyl-1,3-pentylene)acetal,
9α,11β-dichloro-6α-fluoro-16α,17α,21,21-tetrahydroxypregna-1,4-diene-3,20-dione-16,17-acetonide-21,21-(2,4-dimethyl-1,3-pentylene)acetal,
9α,11β-dichloro-6α-fluoro-16α,17α,21,21-tetrahydroxypregna-1,4-diene-3,20-dione-16,17-acetonide-21,21-(2-ethyl-1,3-hexylene)acetal,
9α,11β-dichloro-6α-fluoro-16α,17α,21,21-tetrahydroxypregna-1,4-diene-3,20-dione-16,17-acetonide-21,21-(2-n-propyl-1,3-hexylene)acetal.
9α,11β-dichloro-6α-fluoro-16α,17α,21,21-tetrahydroxypregna-1,4-diene-3,20-dione-16,17-acetonide-21,21-(2-ethyl-1,3-heptylene)acetal,
9α,11β-dichloro-6α-fluoro-16α,17α,21,21-tetrahydroxypregna-1,4-diene-3,20-dione-16,17-acetonide-21,21-(2-n-propyl-1,3-heptylene)acetal,
9α,11β-dichloro-6α-fluoro-16α,17α,21,21-tetrahydroxypregna-1,4-diene-3,20-dione-16,17-acetonide-21,21-(2,4-heptylene)acetal,
9α,11β-dichloro-6α-fluoro-16α,17α,21,21-tetrahydroxypregna-1,4-diene-3,20-dione-16,17-acetonide-21,21-(5-methyl-2,4-hexylene)acetal,
9α,11β-dichloro-6α-fluoro-16α,17α,21,21-tetrahydroxypregna-1,4-diene-3,20-dione-16,17-acetonide-21,21-(3,5-octylene)acetal,
9α,11β-dichloro-6α-fluoro-16α,17α,21,21-tetrahydroxypregna-1,4-diene-3,20-dione-16,17-acetonide-21,21-(2,6-dimethyl-3,5-heptylene)acetal,
9α,11β-dichloro-6α-fluoro-16α,17α,21,21-tetrahydroxypregna-1,4-diene-3,20-dione-16,17-acetonide-21,21-(2-methyl-3,5-nonylene)acetal,
9α-chloro-6α-fluoro-11β,16α,17α,21,21-pentahydroxypregna-1,4-diene-3,20-dione-16,17-acetonide-21,21-(2-methyl-2-sec-butyl-1,3-propylene)acetal,
9α-fluoro-11β,16α,17α,21,21-pentahydroxypregna-1,4-diene-3,20-dione-16,17-acetonide-21,21-(2-ethyl-2-isobutyl-1,3-propylene)acetal,
11β,16α,17α,21,21-pentahydroxypregn-4-ene-3,20-dione-16,17-acetonide-21,21-(2,2-di-n-butyl-1,3-propylene)acetal, 11β,16α,17α,21,21-pentahydroxypregna-1,4-diene-3,20-dione-16,17-acetonide-21,21-(2-ethyl-1,3-butylene)acetal,
6α-chloro-11β,16α,17α,21,21-pentahydroxypregna-1,4-diene-3,20-dione-16,17 -acetonide-21,21-(2ethyl-1,3-heptylene) acetal,
6α,9α-difluoro-11β,16α,17α,21,21-pentahydroxypregna-1,4-diene-3,20-dione-16,17-acetonide-21,21-(2,2-dimethyl-1,3-butylene)acetal,
6α-fluoro-11β,16α,17α,21,21-pentahydroxypregna-1,4-diene-3,20-dione-16,17-acetonide-21,21-(2,2-dimethyl-1,3-pentylene) acetal,
6α,9α-difluoro-11β,16α,17α21,21-pentahydroxypregn-4-ene-3,20-dione-16,17-acetonide-21,21-(2,2-dimethyl-1,3-hexylene) acetal,
6α-fluoro-11β,16α,17α,21,21-pentahydroxypregn-4-ene-3,20-dione-16,17-acetonide-21,21-(2,2,4-trimethyl-1,3-pentylene) acetal,
9α,11β-dichloro-6α-fluoro-16α,17α,21,21-tetrahydroxypregna-1,4-diene-3,20-dione-16,17-acetonide-21,21-(2,2,5-trimethyl-1,3-hexylene)acetal,
9α-chloro-6α-fluoro-11β,16α,17α,21,21-pentahydroxypregna-1,4-diene-3,20-dione-16,17-acetonide-21,21-(2,2-dimethyl-1,3-heptylene)acetal, 9α-fluoro-11β,16α, 17α,21,21-pentahydroxypregna-1,4-diene-3,20-dione-16,17-acetonide-21,21-(2-ethyl-2-n-butyl-1,3-butylene) acetal, 11β,16α,17α,21,21-pentyahydroxypregn-4-ene-3,20-dione-16,17-acetonide-21,21-(3-methyl-2,4pentylene)acetal, 11β,16α,17α,21,21-pentahydroxypregna-1,4-diene-3,20-dione-16,17-acetonide-21,21-(3-methyl-2,4-heptylene)acetal, 6α-chloro-11β,16α,17α,21,21-pentahydroxypregna-1,4-diene-3,20-dione-16,17-acetonide-21,21-(4-n-propyl-3,5-heptylene)acetal, 6α,9α-difluoro-11β,16α,17α,21,21-pentahydroxypregna-1,4-diene-3,20-dione-16,17-acetonide-21,21-(5-ethyl-4,6-nonylene) acetal, 60α-fluoro-11β,16α,17α,21,21-pentahydroxypregna-1,4-diene-3,20-dione-16,17-acetonide-21,21-(2-methyl-4-ethyl-3,5-octylene)acetal, 9α,11β-dichloro-6α-fluoro-16α,17α,21,21-tetrahydroxypregna-1,4-diene-3,20-dione-16,17-acetonide-21,21-(5-ethyl-4,6-decylene)acetal, 6α,9α-difluoro-11β16α,17α,21,21-pentahydroxypregna-1,4-diene-3,20-dione-16,17-acetonide-21,21-(3,3-dimethyl-2,4-pentylene)acetal, 60α-fluoro-11β,16α,17α,21,21-pentahydroxypregna-1,4-diene-3,20-dione-16,17-acetonide-21,21-(3,3-dimethyl-2,4-hexylene) acetal, 6α,9α-difluoro-11β,16α,17α,21,21-pentahydroxypregn-4-ene-3,20-dione-16,17-acetonide-21,21-(2,2,5-trimethyl-2,4-hexylene)acetal, 6α-fluoro-11β,16α,17α,21,21-pentahydroxypregn-4-ene-3,20-dione-16,17-acetonide-21,21-(3,3-dimethyl-2,4-pentylene)acetal, 9α,11β-dichloro-6α-fluoro-16α,17α,21,21-tetrahydroxypregna-1,4-diene-3,20-dione-16,17-acetonide-21,21-(4,4-dimethyl-3,5-heptylene)acetal; and 9α-chloro-6α-fluoro-11β,16α,17α,21,21-pentahydroxypregna-1,4-diene-3,20-dione-16,17-acetonide-21,21-(2,4,4,7-tetramethyl-3,5-octylene)acetal in addition to compounds previously prepared via Examples 2 and 3.

What is claimed is:
1. A compound of the formula:

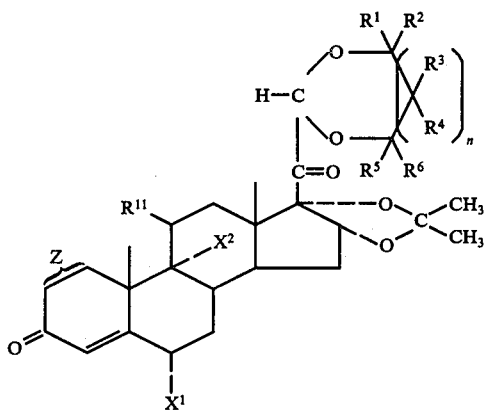

wherein
$n$ is 0 or 1;
each of $R^1 - R^6$ is independently hydrogen or lower alkyl containing 1 to 4 carbon atoms and when $n$ is 0, any two of $R^1$-$R^6$ on adjacent carbon atoms, taken together, are lower alkylene containing 3 to 5 carbon atoms;

$R^{11}$ is chloro or hydroxy;
$X^1$ and $X^2$ are independently hydrogen, chloro or fluoro, with the proviso that when $R^{11}$ is chloro, $X^2$ is chloro; and
Z is a single or double bond.

2. A compound of claim 1 of the formula:

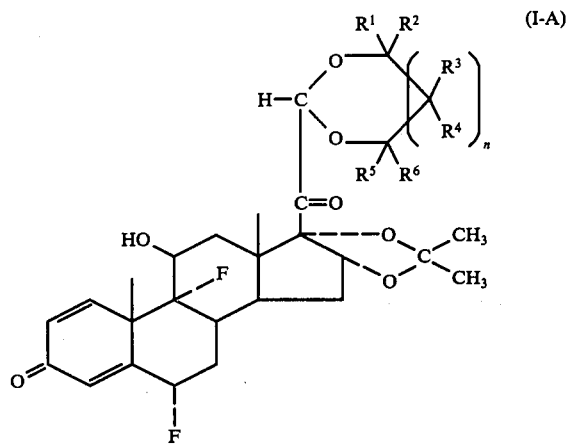

wherein $R^1 - R^6$ and $n$ are as defined in claim 1.

3. A compound of claim 2 wherein all of $R^1 - R^6$ are hydrogen.

4. The compound of claim 3 which is 6α,9α-difluoro-11β,16α,17α,21,21-pentahydroxypregna-1,4-diene-3,20-dione-16,17-acetonide-21,21-ethylene acetal.

5. The compound of claim 3 which is 6α,9α-difluoro-11β,16α,17α,21,21-pentahydroxypregna-1,4-diene-3,20-dione-16,17-acetonide-21,21-(1,3-propylene)acetal.

6. A compound of claim 2 wherein one of $R^1 - R^6$ is lower alkyl and the other R groups are hydrogen.

7. A compound of claim 2 wherein two of $R^1 - R^6$ are independently lower alkyl and the other R groups are hydrogen.

8. The compound of claim 7 which is 60α,9αdifluoro-11β,16α,17α,21,21-pentahydroxypregna-1,4-diene-3,20-dione-16,17-acetonide-21,21-(2,2-dimethyl-1,3-propylene)acetal.

9. A compound of claim 1 of the formula:

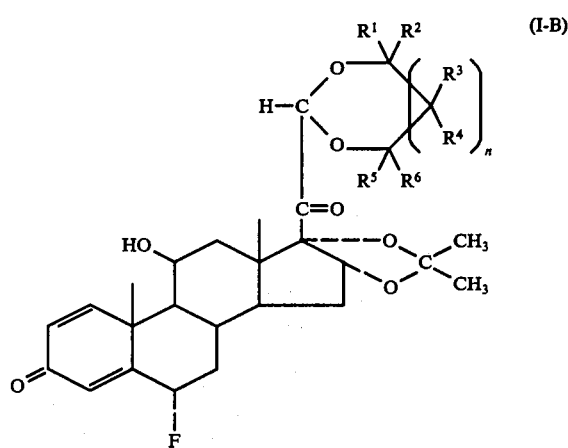

wherein $R^1 - R^6$ and $n$ are as defined in claim 1.

10. A compound of claim 9 wherein all of $R^1 - R^6$ are hydrogen.

11. The compound of claim 10 which is 6α-fluoro-11β,16α,17α,21,21-pentahydroxypregna-1,4-diene-3,20-dione-16,17-acetonide-21,21-ethylene acetal.

12. The compound of claim 10 which is 6α-fluoro-11β,16α,17α,21,21-pentahydroxypregna-1,4-diene-3,20-dione-16,17-acetonide-21,21-(1,3-propylene)acetal.

13. A compound of claim 9 wherein one of $R^1 - R^6$ is lower alkyl and the other R groups are hydrogen.

14. A compound of claim 9 wherein two of $R^1 - R^6$ are independently lower alkyl and the other R groups are hydrogen.

15. A compound of claim 1 of the formula:

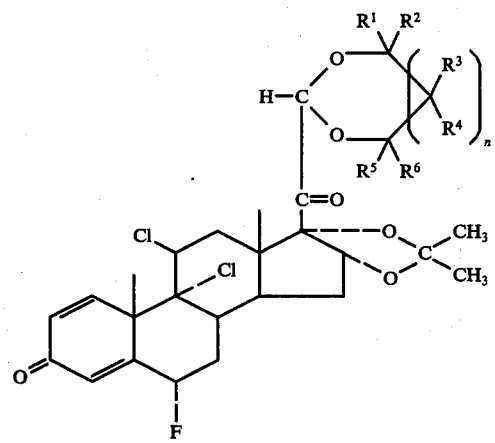
(I-C)

wherein $R^1 - R^6$ and $n$ are as defined in claim 1.

16. A compound of claim 15 wherein all of $R^1 - R^6$ are hydrogen.

17. The compound of claim 16 which is 9α,11β-dichloro-6α-fluoro-16α,17α,21,21-tetrahydroxypregna-1,4-diene-3,20-dione-16,17-acetonide-21,21-ethylene acetal.

18. The compound of claim 16 which is 9α,11β-dichloro-6α-fluoro-16α,17α,21,21-tetrahydroxypregna-1,4-diene-3,20-dione-16,17-acetonide-21,21-(1,3-propylene)acetal.

19. A compound of claim 15 wherein one of $R^1 - R^6$ is lower alkyl and the other R groups are hydrogen.

20. A compound of claim 15 wherein two of $R^1 - R^6$ are independently lower alkyl and the other R groups are hydrogen.

21. A pharmaceutical composition useful for treating inflammatory disorders, comprising a pharmaceutically acceptable non-toxic carrier in admixture with an effective amount of a compound of the formula:

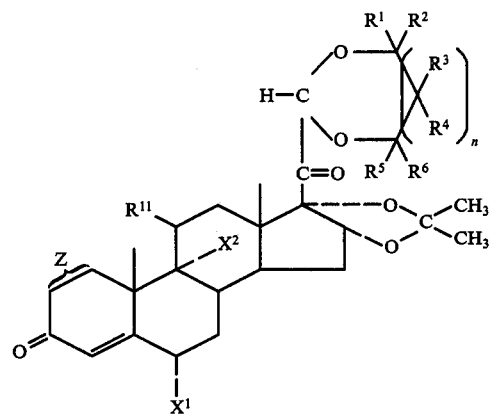
(I)

wherein:
$n$ is 0 or 1;
each of $R^1 - R^6$ is independently hydrogen or lower alkyl containing 1 to 4 carbon atoms and when $n$ is 0, any two of $R^1 - R^6$ on adjacent carbon atoms, taken together, are lower alkylene containing 3 to 5 carbon atoms;
$R^{11}$ is chloro or hydroxy;
$X^1$ and $X^2$ are independently hydrogen, chloro or fluoro, with the proviso that when $R^{11}$ is chloro, $X^2$ is chloro; and
Z is a single or double bond.

22. A method for relieving symptoms associated with inflammatory disorders comprising, administering an effective amount of a compound of the formula:

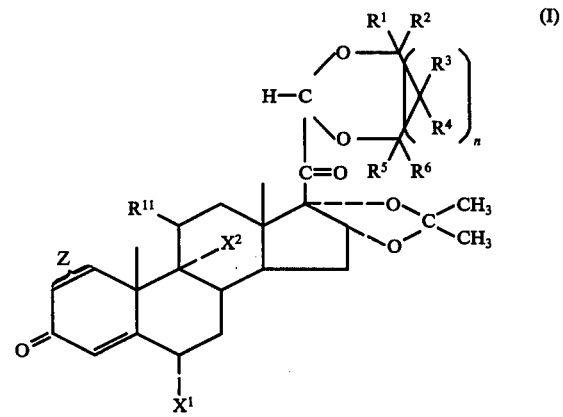
(I)

wherein:
$n$ is 0 or 1;
each of $R^1 - R^6$ is independently hydrogen or lower alkyl containing 1 to 4 carbon atoms and when $n$ is 0, any two of $R^1 - R^6$ on adjacent carbon atoms, taken together, are lower alkylene containing 3 to 5 carbon atoms;
$R^{11}$ is chloro or hydroxy;
$X^1$ and $X^2$ are independently hydrogen, chloro or fluoro with the proviso that when $R^{11}$ is chloro, $X^2$ is chloro; and
Z is a single or double bond; or a pharmaceutical composition same.

* * * * *